United States Patent
Rangarajan et al.

(10) Patent No.: US 11,918,809 B2
(45) Date of Patent: Mar. 5, 2024

(54) SYSTEM AND METHOD FOR AUTOMATIC VAGUS NERVE STIMULATION FOR POST-STROKE REHABILITATION

(71) Applicant: ARIZONA BOARD OF REGENTS ON BEHALF OF ARIZONA STATE UNIVERSITY, Scottsdale, AZ (US)

(72) Inventors: Vishvak Rangarajan, Peoria, AZ (US); Devin Dhooge, Tempe, AZ (US); Kiryl Sheleg, Scottsdale, AZ (US); Nicholas Holmes, Tempe, AZ (US); Jeffrey Kleim, Scottsdale, AZ (US); Bradley Greger, Phoenix, AZ (US); Shivanshi Shukla, Chandler, AZ (US)

(73) Assignee: Arizona Board of Regents on Behalf of Arizona State University, Scottsdale, AZ (US)

( * ) Notice: Subject to any disclaimer, the term of this patent is extended or adjusted under 35 U.S.C. 154(b) by 242 days.

(21) Appl. No.: 17/243,564

(22) Filed: Apr. 28, 2021

(65) Prior Publication Data

US 2021/0339023 A1 Nov. 4, 2021

Related U.S. Application Data

(60) Provisional application No. 63/018,106, filed on Apr. 30, 2020.

(51) Int. Cl.
*A61N 1/36* (2006.01)
*A61N 1/04* (2006.01)
*A61N 5/06* (2006.01)

(52) U.S. Cl.
CPC ....... *A61N 1/36067* (2013.01); *A61N 1/0456* (2013.01); *A61N 1/36025* (2013.01);
(Continued)

(58) Field of Classification Search
CPC .............. A61N 1/36067; A61N 1/3603; A61N 1/0456; A61N 1/36025; A61N 5/0613; A61N 2005/0626
See application file for complete search history.

(56) References Cited

U.S. PATENT DOCUMENTS 8,577,458 B1  11/2013  Libbus et al.
9,089,691 B2   7/2015  Libbus et al.
(Continued)

FOREIGN PATENT DOCUMENTS

KR          102386264 B1    4/2022

OTHER PUBLICATIONS

Kaniusas E, Kampusch S, Tittgemeyer M, et al. "Current Directions in the Auricular Vagus Nerve Stimulation II—An Engineering Perspective." Frontiers in Neuroscience. 2019;13:772. DOI: 10.3389/fnins.2019.00772. PMID: 31396044; PMCID: PMC6667675.

(Continued)

*Primary Examiner* — Ankit D Tejani
*Assistant Examiner* — Joshua Brendon Solomon
(74) *Attorney, Agent, or Firm* — BOOTH UDALL FULLER, PLC

(57) ABSTRACT

A system and method for the automatic stimulation of a vagus nerve for post-stroke rehabilitation is disclosed. The system includes an application subsystem having an electrode positioned to stimulate the vagus nerve and coupled to a user outside of a surgical setting. The system also includes a waveform generator communicatively coupled to the electrode, and a triggering subsystem including a receiver configured to detect the presence of a tag. The triggering subsystem is communicatively coupled to waveform generator and is configured to automatically trigger the stimulation of the vagus nerve upon detecting the presence of the tag. The tag is located proximate a rehabilitation context (Continued)

such that the tag is detected when the user is using the rehabilitation context, resulting in the vagus nerve of the user being automatically stimulated by the electrode in response to the user's post-stroke rehabilitation training.

13 Claims, 2 Drawing Sheets

(52) U.S. Cl.
CPC ......... *A61N 1/3603* (2017.08); *A61N 5/0613* (2013.01); *A61N 2005/0626* (2013.01)

(56) References Cited

U.S. PATENT DOCUMENTS

| | | |
|---|---|---|
| 9,522,272 B2 | 12/2016 | Kilgard et al. |
| 9,662,269 B2 | 5/2017 | Brown et al. |
| 9,839,577 B2 | 12/2017 | Brown et al. |
| 10,010,479 B2 | 7/2018 | Brown et al. |
| 11,311,725 B2 | 4/2022 | Levine et al. |
| 2015/0073505 A1* | 3/2015 | Errico .................. A61N 1/3787 607/60 |
| 2017/0164876 A1* | 6/2017 | Hyde ................... A61B 5/1118 |

OTHER PUBLICATIONS

Schaechter, J., et al. "Will Non-Invasive Vagus Nerve Stimulation Help Improve Upper Limb Function Following Stroke?" Dana Foundation, Clinical Neuroscience Research Grant Program, Dec. 2016.

* cited by examiner

SYSTEM AND METHOD FOR AUTOMATIC VAGUS NERVE STIMULATION FOR POST-STROKE REHABILITATION

RELATED APPLICATIONS

This application claims the benefit of U.S. provisional patent application 63/018,106, filed Apr. 30, 2020 titled "Automatic Vagus Nerve Stimulation Method and Device for Post-Stroke Recovery," the entirety of the disclosure of which is hereby incorporated by this reference.

TECHNICAL FIELD

Aspects of this document relate generally to the automatic stimulation of the vagus nerve for post-stroke rehabilitation.

BACKGROUND

Nearly 800,000 people suffer from a stroke each year in the United States alone, and 40% of those result in a moderate to severe impairment. While 85% of patients are recommended for physical therapy, only one third of them actually receive the therapy required. This physical therapy can be very expensive and lengthy. Rehabilitation can become less effective with increasing time after stroke. In addition to diminishing effectiveness of the rehabilitation, as time goes on the cost to the patient often drastically increases once insurance no longer covers rehabilitation treatment.

Even with delays in starting therapy, though, rehabilitation training combined with vagus nerve stimulation can produce significantly greater forelimb recovery compared to equivalent training without stimulation. Neural stimulation, or neurorehabilitation, is used in treating a variety of neurological diseases such as Parkinson's Disease and migraines. Vagus nerve stimulation during rehabilitation physical training has been shown to lead to better post-stroke outcomes. The vagus nerve is the tenth cranial nerve, and interfaces with the parasympathetic control of the heart, lungs, and digestive tract.

However, despite these benefits, conventional neurorehabilitation has some significant drawbacks. Conventional stimulation devices must be implanted on the patient's vagus nerve, requiring a surgery and its inherent expense and risk. Additionally, conventional stimulation is typically administered by a human operator inside a clinical setting, making it very difficult to use in a home setting.

SUMMARY

According to one aspect, a system for the automatic stimulation of a vagus nerve for post-stroke rehabilitation includes an application subsystem having an electrode in direct contact with a user and positioned to stimulate an auricular branch of the vagus nerve of the user using electrical stimulation. The coupling of the electrode to the user is performed outside of a surgical setting. The system also includes a signal subsystem having a waveform generator with a microcontroller, the waveform generator communicatively coupled to an amplifier, the amplifier communicatively coupled to the electrode of the application subsystem and configured to amplify a waveform generated by the waveform generator, the waveform being square and biphasic. The system further includes a triggering subsystem having a receiver configured to detect the presence of a tag within a threshold distance. The triggering subsystem is communicatively coupled to the signal subsystem and is configured to automatically trigger the generation and amplification of the waveform by the signal subsystem upon detecting the presence of the tag within the threshold distance, the waveform driving the electrode of the application subsystem to stimulate the vagus nerve of the user. The system also includes a wearable casing through which at least the signal subsystem and the triggering subsystem are coupled to the user. The tag is an RFID tag located proximate a rehabilitation context such that the tag is within the threshold distance from the triggering subsystem when the user is using the rehabilitation context for rehabilitation training, resulting in the vagus nerve of the user being automatically stimulated by the application subsystem in response to the user's rehabilitation training. The rehabilitation context is one of a rehabilitation location and a rehabilitation equipment.

Particular embodiments may comprise one or more of the following features. The threshold distance may be less than 30 cm.

According to another aspect of the disclosure, a system for the automatic stimulation of a vagus nerve for post-stroke rehabilitation includes an application subsystem having an electrode positioned to stimulate the vagus nerve of a user. The coupling of the electrode to the user is performed outside of a surgical setting. The system also includes a signal subsystem having a waveform generator communicatively coupled to an amplifier. The amplifier is communicatively coupled to the electrode of the application subsystem and is configured to amplify a waveform generated by the waveform generator. The system further includes a triggering subsystem having a receiver configured to detect the presence of a tag within a threshold distance, the triggering subsystem communicatively coupled to the signal subsystem and configured to automatically trigger the generation and amplification of the waveform by the signal subsystem upon detecting the presence of the tag within the threshold distance, the waveform driving the electrode of the application subsystem to stimulate the vagus nerve of the user. The tag is located proximate a rehabilitation context such that the tag is within the threshold distance from the triggering subsystem when the user is using the rehabilitation context for post-stroke rehabilitation training, resulting in the vagus nerve of the user being automatically stimulated by the application subsystem in response to the user's post-stroke rehabilitation training.

Particular embodiments may comprise one or more of the following features. The electrode may be positioned to stimulate an auricular branch of the vagus nerve of the user. The waveform generator may include a microcontroller. The application subsystem may stimulate the vagus nerve using electrical stimulation, and/or the electrode may be in direct contact with the user. The application subsystem may stimulate the vagus nerve using electromagnetic field stimulation. The system may further include a wearable casing. At least the signal subsystem and/or the triggering subsystem may be coupled to the user through the wearable casing. The tag may be one of an RFID tag, an ultrasonic emitter, and a wireless beacon. The waveform may be square and biphasic. The signal subsystem may be further configured to receive an input specifying at least one of a voltage, a frequency, and a pulse width of the waveform sent to the application subsystem. The application subsystem may be uni-polar. The application subsystem may be one of bi-polar and pseudo bi-polar. The rehabilitation context may be one of a rehabilitation location and a rehabilitation equipment. The threshold distance may be less than 30 cm.

According to yet another aspect of the disclosure, a method for the automatic stimulation of a vagus nerve for post-stroke rehabilitation includes coupling an electrode to a user outside of a surgical setting, the electrode positioned to stimulate the vagus nerve of the user and communicatively coupled to a signal subsystem including a waveform generator and an amplifier. The signal subsystem is configured to drive the electrode using a waveform generated by the waveform generator and amplified by the amplifier. The method further includes positioning a tag proximate a rehabilitation context, and detecting the presence of the tag using a triggering subsystem having a receiver and configured to detect the tag when the tag is within a threshold distance of the receiver. The triggering subsystem is communicatively coupled to the signal subsystem and configured to automatically engage the signal subsystem upon detecting the presence of the tag. The method further includes automatically stimulating the vagus nerve of the user in response to the detection of the tag within the threshold distance of the receive by driving the electrode with the signal subsystem. The tag is positioned proximate the rehabilitation context such that the tag is within the threshold distance of the receiver when the user is using the rehabilitation context for post-stroke rehabilitation training.

Particular embodiments may comprise one or more of the following features. The rehabilitation context may be one of a rehabilitation location and a rehabilitation equipment. The electrode may be positioned to stimulate an auricular branch of the vagus nerve of the user. The electrode may be positioned on the user using transillumination. The tag may be one of an RFID tag, an ultrasonic emitter, and a wireless beacon.

Aspects and applications of the disclosure presented here are described below in the drawings and detailed description. Unless specifically noted, it is intended that the words and phrases in the specification and the claims be given their plain, ordinary, and accustomed meaning to those of ordinary skill in the applicable arts. The inventors are fully aware that they can be their own lexicographers if desired. The inventors expressly elect, as their own lexicographers, to use only the plain and ordinary meaning of terms in the specification and claims unless they clearly state otherwise and then further, expressly set forth the "special" definition of that term and explain how it differs from the plain and ordinary meaning. Absent such clear statements of intent to apply a "special" definition, it is the inventors' intent and desire that the simple, plain and ordinary meaning to the terms be applied to the interpretation of the specification and claims.

The inventors are also aware of the normal precepts of English grammar. Thus, if a noun, term, or phrase is intended to be further characterized, specified, or narrowed in some way, then such noun, term, or phrase will expressly include additional adjectives, descriptive terms, or other modifiers in accordance with the normal precepts of English grammar. Absent the use of such adjectives, descriptive terms, or modifiers, it is the intent that such nouns, terms, or phrases be given their plain, and ordinary English meaning to those skilled in the applicable arts as set forth above.

Further, the inventors are fully informed of the standards and application of the special provisions of 35 U.S.C. § 112(f). Thus, the use of the words "function," "means" or "step" in the Detailed Description or Description of the Drawings or claims is not intended to somehow indicate a desire to invoke the special provisions of 35 U.S.C. § 112(f), to define the invention. To the contrary, if the provisions of 35 U.S.C. § 112(f) are sought to be invoked to define the inventions, the claims will specifically and expressly state the exact phrases "means for" or "step for", and will also recite the word "function" (i.e., will state "means for performing the function of [insert function]"), without also reciting in such phrases any structure, material or act in support of the function. Thus, even when the claims recite a "means for performing the function of . . . " or "step for performing the function of . . . ," if the claims also recite any structure, material or acts in support of that means or step, or that perform the recited function, then it is the clear intention of the inventors not to invoke the provisions of 35 U.S.C. § 112(f). Moreover, even if the provisions of 35 U.S.C. § 112(f) are invoked to define the claimed aspects, it is intended that these aspects not be limited only to the specific structure, material or acts that are described in the preferred embodiments, but in addition, include any and all structures, materials or acts that perform the claimed function as described in alternative embodiments or forms of the disclosure, or that are well known present or later-developed, equivalent structures, material or acts for performing the claimed function.

The foregoing and other aspects, features, and advantages will be apparent to those artisans of ordinary skill in the art from the DESCRIPTION and DRAWINGS, and from the CLAIMS.

BRIEF DESCRIPTION OF THE DRAWINGS

The disclosure will hereinafter be described in conjunction with the appended drawings, where like designations denote like elements, and.

DETAILED DESCRIPTION

Figure 1:
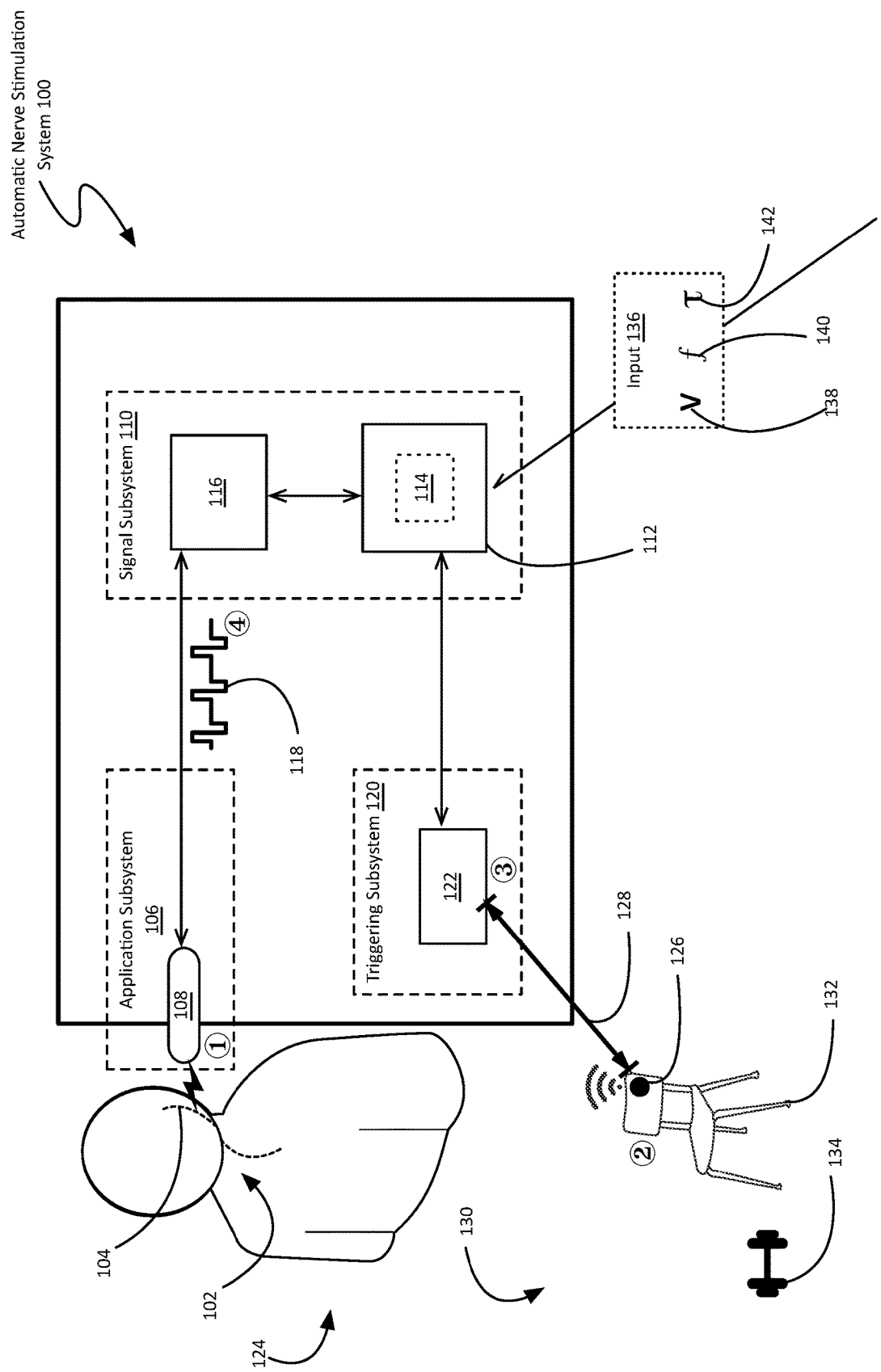
FIG. 1 is a schematic view of an automatic nerve stimulation system.

This disclosure, its aspects and implementations, are not limited to the specific material types, components, methods, or other examples disclosed herein. Many additional material types, components, methods, and procedures known in the art are contemplated for use with particular implementations from this disclosure. Accordingly, for example, although particular implementations are disclosed, such implementations and implementing components may comprise any components, models, types, materials, versions, quantities, and/or the like as is known in the art for such systems and implementing components, consistent with the intended operation.

The word "exemplary," "example," or various forms thereof are used herein to mean serving as an example, instance, or illustration. Any aspect or design described herein as "exemplary" or as an "example" is not necessarily to be construed as preferred or advantageous over other aspects or designs. Furthermore, examples are provided solely for purposes of clarity and understanding and are not meant to limit or restrict the disclosed subject matter or relevant portions of this disclosure in any manner. It is to be appreciated that a myriad of additional or alternate examples of varying scope could have been presented, but have been omitted for purposes of brevity.

While this disclosure includes a number of embodiments in many different forms, there is shown in the drawings and will herein be described in detail particular embodiments with the understanding that the present disclosure is to be considered as an exemplification of the principles of the disclosed methods and systems, and is not intended to limit the broad aspect of the disclosed concepts to the embodiments illustrated.

Nearly 800,000 people suffer from a stroke each year in the United States alone, and 40% of those result in a moderate to severe impairment. While 85% of patients are recommended for physical therapy, only one third of them actually receive the therapy required. This physical therapy can be very expensive and lengthy. Rehabilitation can become less effective with increasing time after stroke. In addition to diminishing effectiveness of the rehabilitation, as time goes on the cost to the patient often drastically increases once insurance no longer covers rehabilitation treatment.

Even with delays in starting therapy, though, rehabilitation training combined with vagus nerve stimulation can produce significantly greater forelimb recovery compared to equivalent training without stimulation. Neural stimulation, or neurorehabilitation, is used in treating a variety of neurological diseases such as Parkinson's Disease and migraines. Vagus nerve stimulation during rehabilitation physical training has been shown to lead to better post-stroke outcomes. The vagus nerve is the tenth cranial nerve, and interfaces with the parasympathetic control of the heart, lungs, and digestive tract.

However, despite these benefits, conventional neurorehabilitation has some significant drawbacks. Conventional stimulation devices must be implanted on the patient's vagus nerve, requiring a surgery and its inherent expense and risk. Additionally, conventional stimulation is typically administered by a human operator inside a clinical setting, making it very difficult to use in a home setting.

Contemplated herein is a system and method for automatic stimulation of the vagus nerve for post-stroke recovery. Unlike conventional vagus stimulation devices and methods, the system contemplated herein does not require an electrode to be surgically implanted, making the contemplated method of enhanced rehabilitation more logistically and financially accessible to a greater number of people. The contemplated system removes the need for surgery by stimulating the auricular branch of the vagus nerve in the patient using percutaneous electrical nerve stimulation, according to various embodiments. The auricular nerve branches out to the external ear. It has been shown that stimulating the auricular branch of the vagus nerve lowers the heart rate of the user, which is a widely approved indicator that the vagus nerve has been activated. Using auricular nerve stimulation with an automated component may result in improved outcomes from stroke rehabilitation training, by increasing availability of the treatment, and also making it usable outside of clinical settings.

Using vagal nerve stimulation long after the stroke can enhance recovery by generating repeated, temporally precise, consistent engagement of pro-plasticity neuromodulator circuits to reinforce rehabilitation-related neural activity. Unlike conventional systems, the system contemplated herein enhances the rehabilitation treatment by performing the stimulation at the same time the stroke patient is making a movement during their rehabilitation training.

Additionally, the system and method contemplated herein is able to perform the stimulation concurrently with training movement automatically, further increasing the availability of the treatment at a lower cost to the patient. The system is able to automate the stimulation using one or more tags that are detected by a receiver that triggers the stimulation. According to various embodiments, the receiver will induce stimulation when it is in proximity to its respective tag, which is located in the space where the patient performs therapy, or on the equipment being used. This allows vagus nerve stimulation to automatically occur in the intervals during which the patient performs therapy. The automatic component also reduces the need for a therapist to be present during therapy and allows the patient more flexibility for performing vagus nerve stimulation at home.

The contemplated system is closed-loop, so it stimulates the vagus nerve in response to the stroke patient's movements and/or engaging in rehabilitation training. This is advantageous over conventional, open-loop systems which stimulate the vagus nerve in response to a command from a therapist. A close-loop system such as the system contemplated herein removes the need for a therapist to accompany a stroke patient during their rehabilitation, making it possible for stroke patients to perform this neurostimulation-enhanced rehabilitation therapy at home or some other convenient location.

It should be noted that while the following disclosure is made in the context of using the contemplated system and method for post-stroke recovery, and in the context of stimulating the vagus nerve, those skilled in the art will recognize that the system and method contemplated herein may be adapted for use in treating other conditions that may be sensitive to neural stimulation, as well as for stimulating other nerves.

FIG. 1 is a schematic view of a non-limiting example of an automatic nerve stimulation system 100 for the post-stroke rehabilitation of a user 124 (e.g. stroke patient). As shown, the automatic nerve stimulation system 100 (hereinafter "ANS system" or "system") comprises three subsystems: an application subsystem 106, a signal subsystem 110, and a triggering subsystem 120, each of which will be discussed below. As will be discussed, this system 100 is able to automatically stimulate the vagus nerve 102 of the user 124 concurrently with the actual performance of rehabilitation therapy or exercises, resulting in outcomes superior to rehabilitation without neurostimulation.

The application subsystem 106 is responsible for performing the actual stimulation of the vagus nerve 102. As shown, the application subsystem 106 comprises at least one electrode 108, which is communicatively coupled to a signal subsystem 110, discussed below. Advantageous over conventional neurostimulation systems, the ANS system 100 contemplated herein comprises electrodes 108 that do not require surgical implantation, meaning the electrodes 108 may be attached to the user 124 outside of a surgical setting. In some embodiments, the electrode 108 may be in direct contact with the user 124 (e.g. skin, vagus nerve, etc.), where it delivers electrical stimulation that activates the vagus nerve 102. In other embodiments, the electrode 108 may stimulate the vagus nerve 102 using an electromagnetic field (e.g. pulsed radiofrequency, etc.), which may be performed with electrodes 108 placed in proximity to the nerve 102, but not necessarily in direct contact.

As discussed above, the ANS system 100 is able to be coupled to the user 124 outside of a surgical setting by positioning the electrode 108 such that an auricular branch 104 of the vagus nerve 102 is targeted. In the context of the present description and the claims that follow, to be "outside a surgical setting" refers to procedures that do not require a sterile operating environment. Examples include, but are not limited to, electrode attachments performed on an outpatient basis at a doctor's office or clinic, and attachments performed by someone other than an medical professional. For example, in one embodiment, the electrode may be installed by the user 124 or someone assisting them, and the installation may be guided using an app running on a smart phone or tablet (e.g. assisted targeting using augmented reality, telemedicine, real-time heart rate readings provided to the app by a smart watch or other connected device to determine if the vagus nerve is being engaged, etc.).

The electrode(s) 108 of the application subsystem 106 could be of various forms. In some embodiments, the electrode 108 may be of a contact, non-penetrating type, meaning attached to the user 124 (e.g. skin, etc.) by mechanical methods or adhesive. In some embodiments, the electrode 108 is uni-polar, having no or distant return, while in other embodiments it is bi-polar, having electrode and return pairs. In still other embodiments, the electrode 108 is pseudo bi-polar, having multiple electrodes working with a single return. It should be noted that while much of the discussion herein is made speaking of a singular electrode 108, that electrode 108 may refer to multiple electrodes, including but not limited to uni-polar, bi-polar, and pseudo bi-polar configurations.

In other embodiments, the electrode 108 may be of a contact and penetrating type, meaning the electrode 108 is inserted into tissue such that they are in or near the vagus nerve 102 in uni-polar, bi-polar, or pseudo bi-polar configurations. In still other embodiments, the electrode 108 may be of a non-contact field type, meaning that an insulator or air-gap prevents direct flow of electrical current. Instead, energy is conveyed to the tissue/nerve via electromagnetic field effects and volume conduction.

The signal subsystem 110 is responsible for generating the waveform 118 that will be applied to the user 124 through the application subsystem 106. According to various embodiments, the signal subsystem 110 comprises a waveform generator 112. In some embodiments, the waveform generator 112 may comprise a microcontroller 114, such as a single board microcontroller 114 like an Arduino. Other embodiments may employ more sophisticated or robust waveform generators 112, which may provide a wider range of frequencies with greater precision, but at a much higher cost.

In some embodiments, the waveform 118 generated may be a square waveform 118. In some embodiments, the square-wave may be uni-phasic, while in other embodiments, it may be multi-phasic. In other embodiments, a different waveform 118 may be used to achieve a different effect in the stimulation of the user's vagus nerve 102 (e.g. sinusoidal waveforms, stochastic or arbitrary waveforms, etc.).

The signal subsystem 110 is communicatively coupled to the electrode 108 of the application subsystem 106. In some embodiments, the signal subsystem 110 also comprises an amplifier 116, such as an op-amp, and the waveform generator 112 is coupled to the electrode 108 through that amplifier 116. The output signal from the microcontroller 114 may be sent through the amplifier 116 before being sent to the electrode 108. In some embodiments, the voltage of this amplified signal may be modulated using a potentiometer. As a specific, non-limiting example, in one embodiment, the signal subsystem 110 may be configured to drive the electrode 108 with a biphasic square waveform 118 of around 2-10V and a frequency of 25-30 Hz.

In some embodiments, the stimulation waveform voltage 138, frequency 140, and/or pulse width 142 may be adjustable through an input 136 provided to the system 100, either through an interface localized on the system 100, or programmatically through another system communicatively coupled (e.g. wireless, wired, over the Internet, through a cloud provider, etc.) to the ANS system 100. Examples include, but are not limited to, an app running on a smart phone, a web interface served by the ANS system 100 to the local network, and the like.

The triggering subsystem 120 is responsible for determining when the user 124 is engaged in rehabilitation training and subsequently triggering the signal subsystem 110 (to which it is communicatively coupled) to drive the application subsystem 106 to stimulate the user's vagus nerve 102. According to various embodiments, the triggering subsystem 120 comprises a receiver 122 configured to detect the presence of a tag 126 when the tag 126 is within a threshold distance 128 from the receiver 122.

In some embodiments, the receiver 122 may be configured for use with passive, non-powered tags 126, such as passive RFID tags that emit a signal once energized by another signal. In other embodiments, the receiver 122 may be configured for use with active, powered tags 126, as is known in the art. It should be noted that while much of the following discussion will be done in the context of a singular tag 126, the ANS system 100 may be used with multiple tags 126, according to various embodiments.

The tag 126 is placed inside, on, or at least proximate a rehabilitation context 130. A rehabilitation context 130 is a rehabilitation location 132 or object (e.g. rehabilitation equipment 134, etc.) that is employed for or otherwise associated with, the post-stroke rehabilitation training, and whose nature is such that a tag 126 may be placed on or near said context 130 so it will be within the threshold distance 128 of the receiver 122 when the user 124 is engaged in the training. In some embodiments, the threshold distance 128 may be on the order of 10 cm, while in other embodiments, the threshold distance 128 may be between 10 cm and 30 cm. In still other embodiments, the threshold distance 128 may be greater than 30 cm. Those skilled in the art will recognize that the threshold distance 128 may be limited by the type of receiver 122 and/or tag 126 used, and/or may be deliberately limited by the way the receiver 122 and/or tag 126 are configured (e.g. power level of an active tag, etc.).

In some embodiments, the receiver 122 is an RFID reader and the tag 126 is an RFID tag. However, other embodiments may employ other technologies that are able to detect the presence of a tag or beacon. Examples include, but are not limited to, wireless (e.g. Low energy Bluetooth, WIFI, etc.) beacons, ultrasonic emitters or transducers, and the like. In other embodiments, the triggering subsystem 120 may be activated upon a determination that the user 124 is engaged in rehabilitation training based on an observation or reading performed by a sensor or diagnostic equipment that may be associated with the rehabilitation training. Examples include, but are not limited to, electrophysiological sensors (e.g. EMG, ECG, EEG, etc.), mechanical sensors (e.g. blood pressure, respiration sensors, etc.), movement sensors, behavioral sensors, video-based diagnostic systems, machine vision, and the like In one specific, non-limiting embodiment, the triggering subsystem 120 of the ANS system 100 comprises an ID-20LA RFID reader (i.e. receiver 122), which has a reading range of around 8-12 cm, reading tags 126 at a frequency of 125 kHz. Setting the reader to "Magnetic Emulation" mode makes the ID-20LA output a small voltage from one of its pins when it is in range of a frequency-compatible RFID tag 126. That pin is communicatively coupled to the waveform generator 112 of the signal subsystem 110, such that the small voltage output in response to detecting the tag 126 results in the signal subsystem 110 driving the application subsystem 106.

According to various embodiments, a method for the automatic stimulation of a vagus nerve 102 for post-stroke rehabilitation begins with the coupling of an electrode 108 to a user 124 outside of a surgical setting. See 'circle 1'. In some embodiments, The electrode may be mounted near the auricular branch 104 of the vagus nerve 102 using a method called transillumination. In the context of the present description, transillumination refers to the transmission of light through tissues of the body, a simple and inexpensive method of imaging. As a specific, non-limiting example, in one embodiment, the electrode 108 is made of titanium and has a diameter of 0.125 mm and a length of 1 mm.

Before stimulation can be automatically triggers, the tag 126 must be put into place. At least one tag 126 is placed proximate a rehabilitation context 130, positioned such that the tag 126 will be within the threshold distance 128 of the receiver 122 when the user 124 is using the rehabilitation context 130 for post-stroke rehabilitation training. See 'circle 2'. Examples of rehabilitation training include, but are not limited to, constraint induced movement therapy (CIMT), task-specific training, strength training, mirror therapy, and other forms of rehabilitation training known in the art.

Examples of a rehabilitation context 130 include, but are not limited to, a rehabilitation location 132 (e.g. a room, a chair, a bench, a track, etc.), and a rehabilitation equipment 134 (e.g. weights, hand rails, exercise mats, etc.). As a specific, non-limiting example, tags may be spaced evenly across a tabletop at 15" intervals, such that when the ANS system 100, which may be coupled to the user's arm (see FIG. 2, for example), enters the tabletop workspace to perform a motor rehabilitation task, the system 100 will be triggered.

According to various embodiments, the ANS system 100 is coupled to the user 124, so the receiver 122 will be predictably close to the user when training. For example, in one embodiment, at least the signal subsystem 110 and the triggering subsystem 120 are coupled to the user 124 through a wearable casing, which will be discussed further with respect to FIG. 2, below.

Next, the tag 126 is detected by the receiver 122 once it is within the threshold distance 128 of the receiver 122. See 'circle 3'. As discussed above, the triggering subsystem 120 is communicatively coupled to the signal subsystem 110, and is configured to automatically engage the signal subsystem 110 upon detecting the presence of the tag 126.

Finally, the vagus nerve 102 is automatically stimulated in response to the detection of the tag 126 within the threshold distance 128. See 'circle 4'. One novel aspect of the contemplated system 100 and method is that it stimulates the auricular branch 104 of the vagus nerve 102 in response to the user 124 engaging in rehabilitation training without requiring further input. This is advantageous over conventional vagus nerve systems which are "open-loop", meaning they do not stop stimulating the vagus nerve 102. The contemplated system 100 is closed-loop, meaning that it will automatically stimulate in response to a user behavior, which results in greater outcomes from rehabilitation training.

As a specific but non-limiting example of the type of output a contemplated ANS system 100 may create, the resulting output from the electrode 108 may range from 1-10V, with a current ranging from 2-10 mA. Patient comfort may be facilitated by holding the waveform frequency at approximately 25 Hz, and keeping the overall system weight below 100 g, according to various embodiments.

Figure 2:
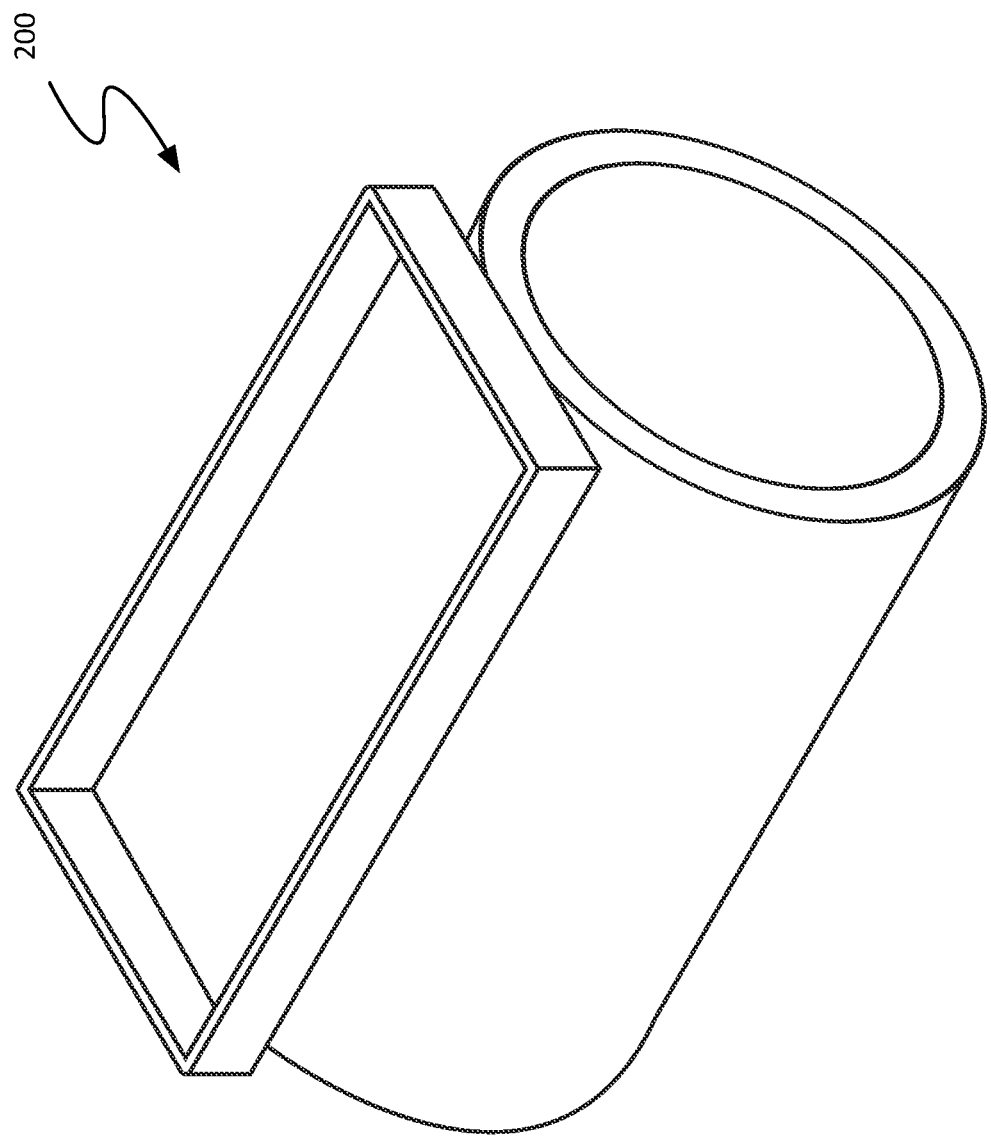
FIG. 2 is a perspective view of a wearable casing for an automatic nerve stimulation system.

FIG. 2 is a perspective view of a non-limiting example of a wearable casing 200 for an automatic nerve ANS system 100. In some embodiments, the ANS system 100 may be mounted to the patient's wrist using a wearable casing 200. In other embodiments, the ANS system 100 may be coupled to the user on their arm, waist (e.g. belt, etc.), back (e.g. backpack, etc.), and other parts of a patient's body, including but not limited to an article of clothing incorporating the various subsystems of the ANS system 100. FIG. 2 shows a non-limiting example of a casing for holding the triggering (e.g. RFID reader, etc.) and signal (e.g. microcontroller 114 waveform generator 112, amplifier 116, etc.) subsystems, along with a power supply (e.g. battery, etc.). In some embodiments, a typical battery life may be between 2 and 4 hours. In other embodiments, the ANS system 100 may be attached to a separate power supply (e.g. mains power, power provided by the rehabilitation context 130, etc.).

According to various embodiments, the system 100 is made safe by ensuring that the Shannon Criteria, a relationship between the charge density per phase and the charge per phase, is satisfied. In other embodiments, the system 100 may be in compliance with ISO standards for stimulation, including electromagnetic field stimulation Where the above examples, embodiments and implementations reference examples, it should be understood by those of ordinary skill in the art that other electrodes, waveforms, waveform generators, receivers, and tags could be intermixed or substituted with those provided. In places where the description above refers to particular embodiments of systems and methods for automatic vagus nerve stimulation, it should be readily apparent that a number of modifications may be made without departing from the spirit thereof and that these embodiments and implementations may be applied to other neurorehabilitation technologies as well. Accordingly, the disclosed subject matter is intended to embrace all such alterations, modifications and variations that fall within the spirit and scope of the disclosure and the knowledge of one of ordinary skill in the art.

What is claimed is:

1. A system for the automatic stimulation of a vagus nerve for post-stroke rehabilitation, comprising:
    an application subsystem comprising an electrode positioned to stimulate the vagus nerve of a user, the coupling of the electrode to the user performed outside of a surgical setting;
    a signal subsystem comprising a waveform generator communicatively coupled to an amplifier, the amplifier communicatively coupled to the electrode of the application subsystem and configured to amplify a waveform generated by the waveform generator; and
    a triggering subsystem comprising a receiver configured to detect the presence of a tag within a threshold distance, the triggering subsystem communicatively coupled to the signal subsystem and configured to automatically trigger the generation and amplification of the waveform by the signal subsystem upon detecting the presence of the tag within the threshold distance, the waveform driving the electrode of the application subsystem to stimulate the vagus nerve of the user;
    wherein the tag is located proximate a rehabilitation context such that the tag is within the threshold distance from the triggering subsystem when the user is using the rehabilitation context for post-stroke rehabilitation training, resulting in the vagus nerve of the user being automatically stimulated by the application subsystem in response to the user's post-stroke rehabilitation training.

2. The system of claim 1, wherein the electrode is positioned to stimulate an auricular branch of the vagus nerve of the user.

3. The system of claim 1, wherein the waveform generator comprises a microcontroller.

4. The system of claim 1, wherein the application subsystem stimulates the vagus nerve using electrical stimulation, the electrode being in direct contact with the user.

5. The system of claim 1, wherein the application subsystem stimulates the vagus nerve using electromagnetic field stimulation.

6. The system of claim 1, further comprising a wearable casing, wherein at least the signal subsystem and the triggering subsystem are coupled to the user through the wearable casing.

7. The system of claim 1, wherein the tag is one of an RFID tag, an ultrasonic emitter, and a wireless beacon.

8. The system of claim 1, wherein the waveform is square and biphasic.

9. The system of claim 1, wherein the signal subsystem is further configured to receive an input specifying at least one of a voltage, a frequency, and a pulse width of the waveform sent to the application subsystem.

10. The system of claim 1, wherein the application subsystem is uni-polar.

11. The system of claim 1, wherein the application subsystem is one of bi-polar and pseudo bi-polar.

12. The system of claim 1, wherein the rehabilitation context is one of a rehabilitation location and a rehabilitation equipment.

13. The system of claim 1, wherein the threshold distance is less than 30 cm.

* * * * *